United States Patent [19]
Andersson

[11] 4,221,015
[45] Sep. 9, 1980

[54] TOOTH-CLEANING DEVICE

[76] Inventor: Bror A. E. Andersson, Österängsvägen 24, S-180, 10 Enebyberg, Sweden

[21] Appl. No.: 20,018

[22] Filed: Mar. 13, 1979

[30] Foreign Application Priority Data

Mar. 13, 1978 [SE] Sweden ................................ 7802828

[51] Int. Cl.³ .......................... A47K 7/02; A47L 13/46
[52] U.S. Cl. ............................... 15/244 R; 15/167 R; 132/84 R
[58] Field of Search ............ 15/244 R, 244 C, 167 R, 15/167 A, 104.94; 132/84 R, 84 A; 401/261

[56] References Cited

U.S. PATENT DOCUMENTS

| 3,087,183 | 4/1963 | Semon | 15/244 R |
| 3,242,519 | 3/1966 | Murray | 15/244 R |
| 3,458,268 | 7/1969 | Wozab et al. | 401/261 |

FOREIGN PATENT DOCUMENTS

| 546136 | 6/1942 | United Kingdom | 15/244 R |
| 636835 | 5/1950 | United Kingdom | 15/244 R |

*Primary Examiner*—Leonard D. Christian
*Attorney, Agent, or Firm*—Young & Thompson

[57] ABSTRACT

A tooth cleaning device comprises a biting bit of an elastically yieldable cellular material and has a slit or groove obtained by means of cutting tools, so that the opposing walls of the slit or groove will act as scrubbing means when a person is chewing with his teeth in the slit or groove.

2 Claims, 13 Drawing Figures

TOOTH-CLEANING DEVICE

The present invention relates to a tooth-cleaning device comprising a biting bit which has a pair of opposing side walls provided with scrubbing or brushing means. If a person bites down between the side walls and performs a chewing motion between said walls, the scrubbing or brushing means will work on the teeth with a cleaning action.

A plurality of biting bits with this function are known in different embodiments, inter alia through the following patent specifications: British Pat. Nos. 546 136, 636 835, German Pat. No. 159 263 and U.S. Pat. No. 3,163,874, 3,769,652.

Common for all the known biting bits is that they are comparatively complicated to manufacture and thus have correspondingly high manufacturing costs. This means that such a chewing toothbrush is normally used a number of times before it is regarded as being sufficiently used to justify the cost of procuring it.

Such a tooth-cleaning device is a good aid per se, inter alia in medical care, in the cases where the patient has difficulty in looking after cleaning his teeth himself with a conventional toothbrush. In such cases, the conventional toothbrush must be handled by the nursing staff. The work thus requires extra labour by the nursing staff and takes time which could be used for other purposes. On the other hand, if the patient has access to a chewing toothbrush of the kind in question, the patient can do the tooth-cleaning himself by a simple chewing motion. Since the known chewing toothbrushes must normally be used a plurality of times because their procurement cost is relatively high, they require cleaning after use, which means extra work for the staff.

Against the background of the above, it is apparent that there is a need for a tooth-cleaning device of the chewing toothbrush type which can be manufactured in such a cheap fashion that the procurement cost does not need to be so high that it does not allow the chewing toothbrush to be thrown away after being used a single time. The labour time and cost of cleaning the chewing toothbrush after use is thus eliminated.

The object of the present invention is therefore to provide a tooth-cleaning device such that it can be manufactured to a cost which is so low in relation to the known chewing toothbrushes that the device can be thrown away after using once without economic inexpediency.

This is achieved according to the invention by a tooth-cleaning device having the distinguishing features disclosed in the accompanying claims. By selecting a particular material for the biting bit, and working on this material in a particular way, the necessary scrubbing or brushing means on each of two opposing side walls in the biting bit can be obtained in an extremely simple fashion.

The invention is based on the knowledge that if a cellular, elastically yielding material, preferably cellular plastics or similar material, is worked on with cutting tools, the cut surface obtained will have a superficial structure which, when pressed against the tooth executing an upwards-downwards motion, will scrub the tooth for cleaning it.

From cellular plastics known per se, a foamed polyolefin, e.g. polyethylene, polypropene or polystyrene can be used to advantage. Experiments carried out have shown that a cross-linked material functions satisfactorily for the purpose. The material can be produced by direct foaming, whereby the cellular size should be within the range of 1–20 mm, or by compressing cellular plastics balls having a diameter in the range of 1–20 mm. The density of the material is suitably in the range of 100–500 kg/m$^3$ and its ability to regain its shape must be high, i.e. the permanent deformation after loading must be low. If a biting bit of such cellular plastics is subjected to cutting machining with the object of providing two opposing cut surfaces, a more or less rough surface structure is obtained at each cut surface, with cavities and intermediate separating walls and their cut edges obtained by cutting through the cells in the area of the cutting plane. To a certain extent, these edges are elastically yielding when they are subjected to compression and/or bending forces.

In its most simple embodiment, the cellular plastics biting bit is provided with a slit of such depth that the teeth to their full length can bite down into the slit so far that the upper or lower side of the biting bit comes into contact with the gum. The teeth thus force out the opposing side walls of the slit, said walls coming into engagement with a certain elastic pressure against the sides of the teeth. If, by means of a chewing motion, the teeth now execute an upwards-downwards movement relative to the two cut surfaces, i.e. the side walls of the slit, said edges of the cell walls will scrub against the sides of the teeth to clean them. Practical tests have shown that this embodiment gives a satisfactory cleaning effect.

In some cases, reinforcement of the cleaning effect can be achieved by combining the cellular plastics material with fibres having greater stiffness than the cellular plastics material, these fibres being mixed into the cellular plastics material. When such a material is cut through, the cut surfaces will thus contain the ends of cut-off fibres, and these fibre ends will thus provide a reinforced scrubbing or brushing action.

The biting bit in the device according to the invention is suitably provided with a projection portion which can be designed alternatively for holding with the fingers while using the biting bit, or for forming a support for the tongue if it is desired to keep the biting bit pressed against the upper or lower row of teeth, this projecting portion being formed integrally with the biting bit. When it is to be held with the fingers, it has the form of a handle or shank.

The tooth-cleaning device consisting of a cellular plastics biting bit and handle can be manufactured in a simple way by stamping or cutting out its form from a web of cellular plastics. The capability of cutting into the material makes it possible to give the biting bit and handle a shape such that it is relatively easy to cut out from the material web in a way resulting in relatively small amounts of waste material.

The tooth-cleaning device according to the invention can thus be manufactured from a relatively cheap material, manufacturing being enabled by means of simple cutting operations to give the tooth-cleaning device a desired shape and for providing one or more pairs of opposing cut surfaces as scrubbing surfaces for cleaning teeth.

Within the scope of the invention, it is possible to make the cut in the biting bit such that the two opposing cut surfaces are mutually spaced at a predetermined distance, although this distance is usually comparatively small and not so large that the teeth do not have satisfactory contact with the cut surfaces during chewing. Alternatively, the cut surfaces can form side walls in a narrow groove where the side walls converge towards the bottom of the groove. The biting bit can be made in different sizes, either so that it substantially covers the whole of the upper or lower row of teeth, substantially half the length of the row of teeth, or only a part of half the length of the row of teeth, and a slit or a narrow groove with said cut surfaces can be made in the upper or lower side of the biting bit, or in both the upper and lower sides.

The main direction of the slit along the biting bit can to advantage be straight when the biting bit is short, i.e. intended for a portion of the row of teeth which is less than half the length of the row of teeth. For longer biting bits, the extension of the slit or groove is more or less curved to suit the curve of the row of teeth.

The cutting plane itself can be flat, but to advantage it can also be zigzag-shaped or corrugated so that the cut surfaces have outstanding ridges and intermediate valleys for more effective adjustment to the convex surface of the teeth.

These and other distinguishing features and advantages of the invention will now be described in more detail while referring to a tooth-cleaning device according to the invention, schematically shown on the accompanying drawings.

Figures 2, 2A:
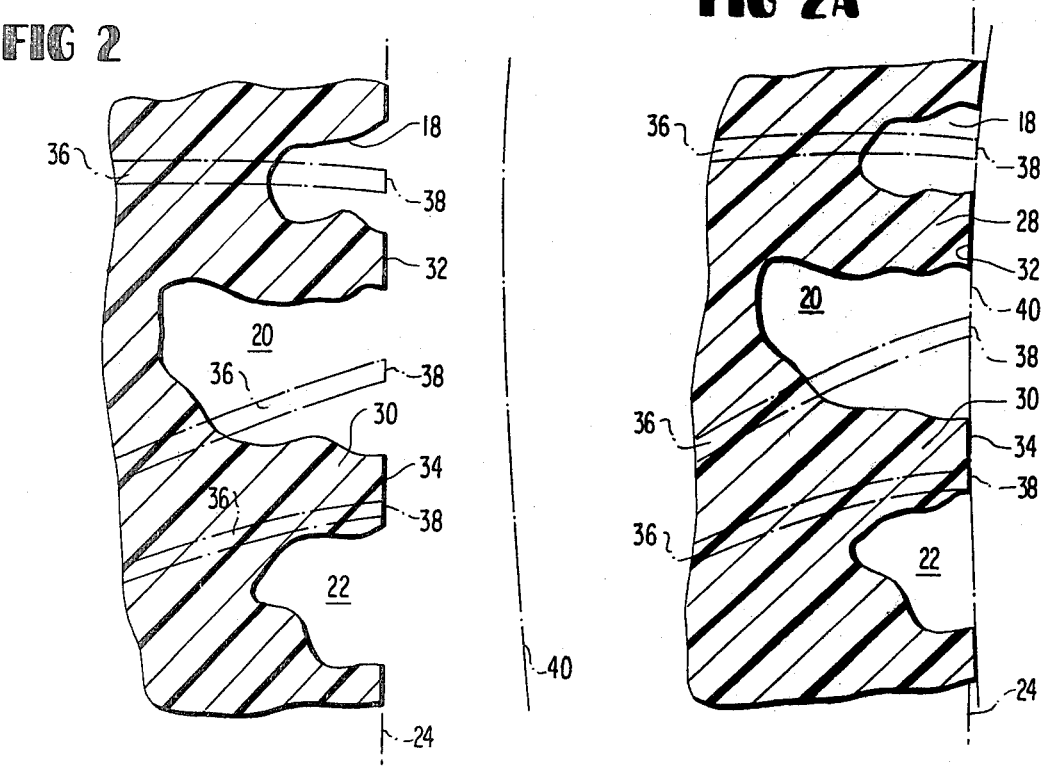
FIG. 2 is a cross-section along the line 2—2 of the cellular plastics block in FIG. 1, a chain-dotted line situated at a distance in front of the cut surface indicating a tooth surface to be cleaned.
Figure 3:
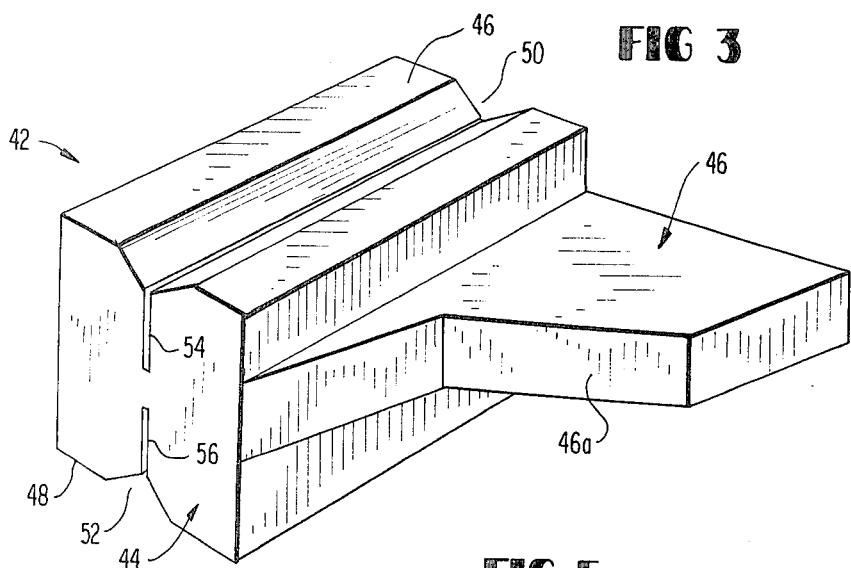
Figure 4:
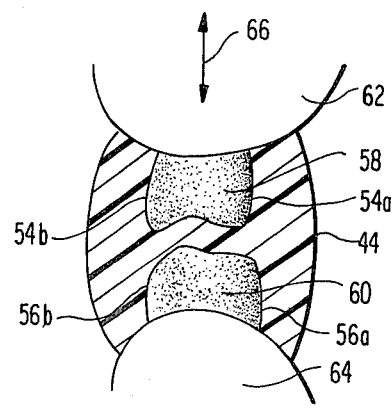
Figure 5:
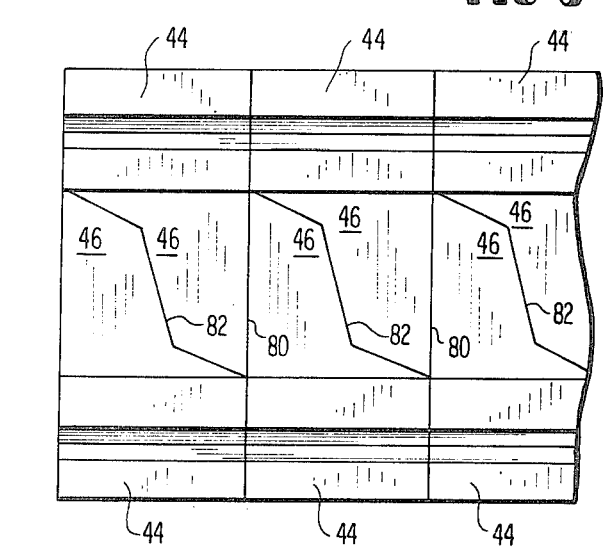
Figure 6:
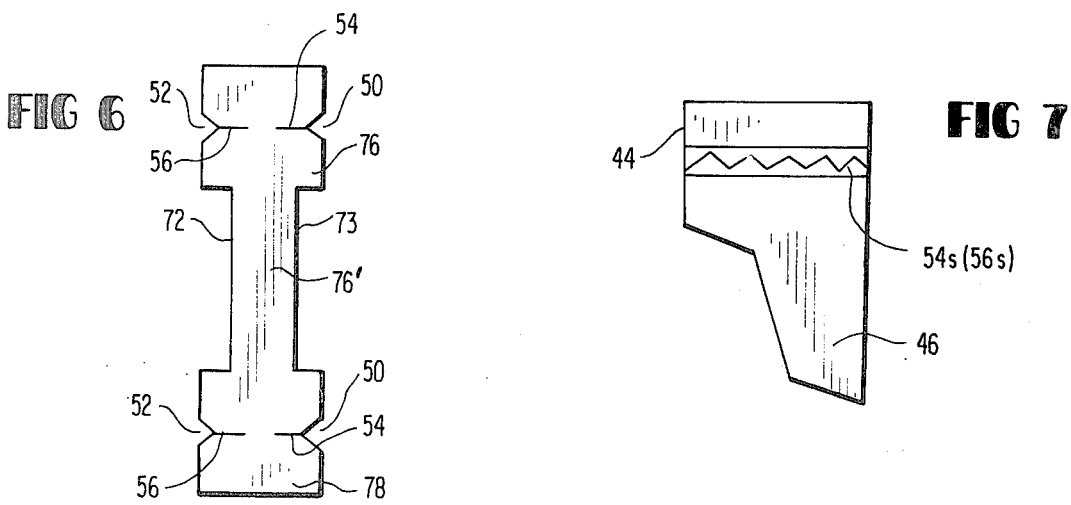
Figure 7:
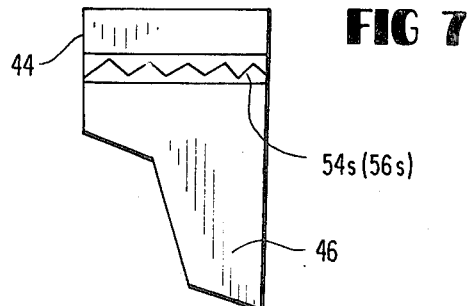
Figure 8:
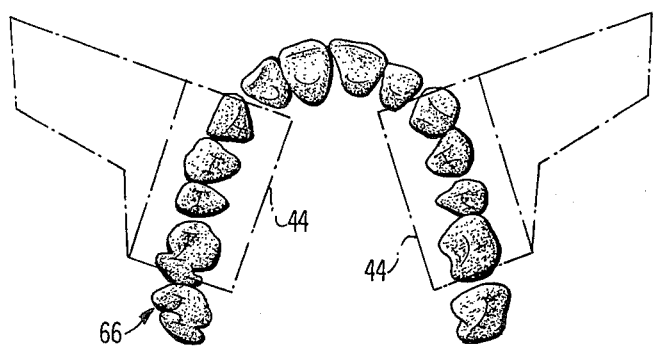
Figure 9:
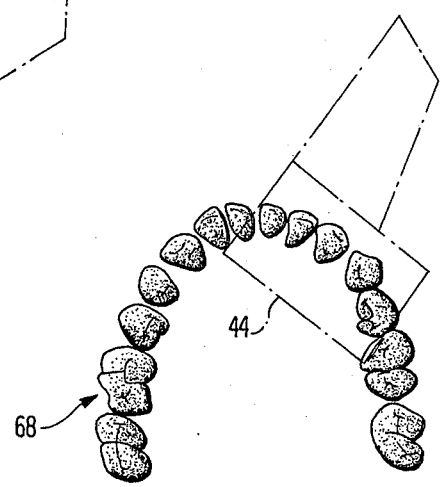
Figure 12:
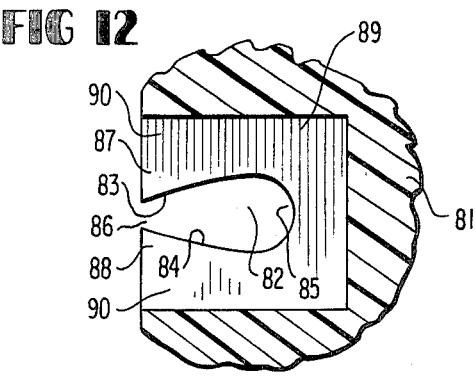
Figure 10:
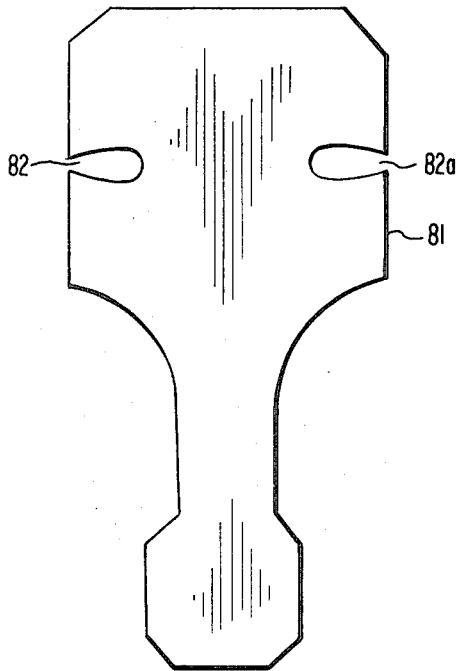
Figure 11:
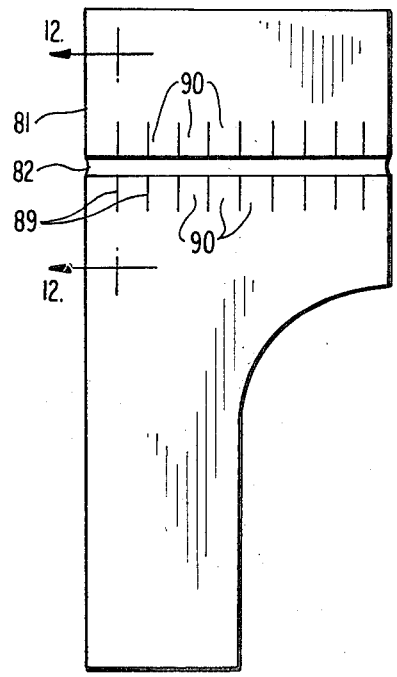

FIG. 2A is the same section as in FIG. 2, the indicated tooth surface being pressed against the cut surface of the block, FIG. 3 is a schematic, perspective view of a tooth-cleaning device according to the invention, with biting bit and handle, FIG. 4 is a schematic picture of two teeth biting down onto slits in the biting bit, FIG. 5 is a side view of a cellular plastics web with cuts for forming a plurality of cleaning devices as shown in FIG. 3, FIG. 6 is an end view of the web in FIG. 5, FIG. 7 is a schematic view which shows a cleaning device according to FIG. 3 with a modified form of the slit, FIGS. 8 and 9 schematically show the cleaning device of FIG. 3 placed in different positions in relation to the row of teeth in the upper and lower jaw, respectively, FIG. 10 is an end view of a modified embodiment, FIG. 11 is a side view of the modified embodiment of FIG. 10, and FIG. 12 is an enlarged sectional detail view along the line 12—12 in FIG. 11.

Figure 1:
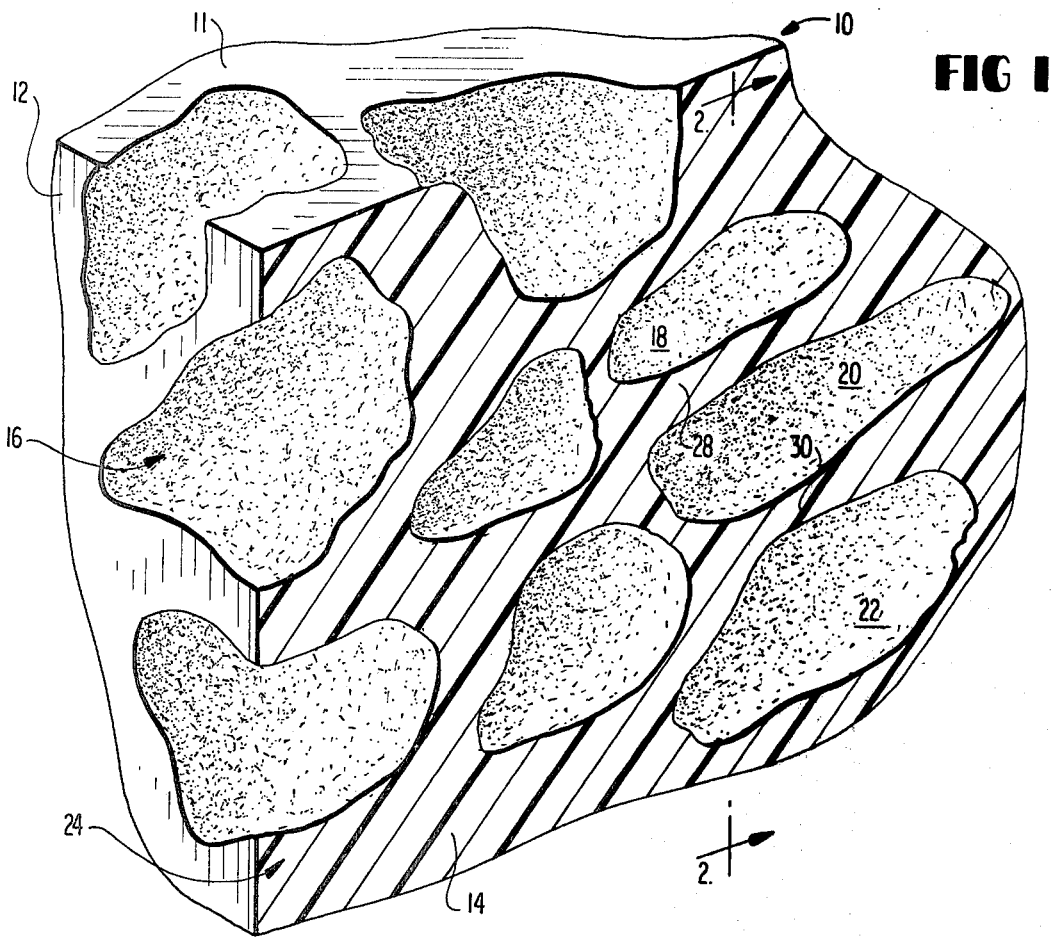
FIG. 1 is a schematic, heavily enlarged, partial, perspective view of the corner portion of a cellular plastics block with a cut surface, obtained by machine cutting, on the front side of the block in the figure.

The elastically deformable cellular plastics block 10 in FIG. 1 suitably consists of a foamed polyolefin such as polyethylene and which can have been formed by compressing cellular plastics balls. The shown corner portion has an upper side 11, an end side 12 and a front side 14. At least the front side 14 consists of a cut surface obtained by cutting tooling, e.g. by means of a knife, a rotating blade or a milling cutter.

The cellular plastics material has a large number of cells or cavities, generally denoted by the numeral 16, while some individual cavities have been denoted by 18, 20 and 22. The material forming the separating wall between the cells is generally denoted by 24, while the separating walls between the cells 18, 20 and 22 are denoted by 28, 30.

As is apparent from FIGS. 2 and 2A, the edges 32,34 of the cut-off separating walls will be in the plane of the cut surface.

Fibres or threads of a material, suitably more difficult to bend than the plastics material in the block, may possibly be mixed in the cellular plastics. These fibres or threads are indicated at 36 by chain-dotted lines and have cut-off ends 38.

In FIGS. 2 and 2A a tooth surface is schematically indicated by a chain-dotted line 40. In FIG. 2 the tooth surface 40 is spaced from the cut surface 24, and in FIG. 2A the cut surface 24 is pressed against the tooth surface 40 with a certain elastic deformation.

If the tooth surface 40 is now caused to move up and down in relation to the cut surface in FIG. 2A, the edges 32,34 which are elastic to a certain extent, will function as scrubbing or brushing means, striving to remove foreign matter from the tooth surface. Practical tests have shown that the cleaning effect is satisfactory. Taking guidance from the above principle for providing cleaning of a tooth surface, a cleaning device 42 can be formed with a biting bit 44 and a handle 46, e.g. of the kind apparent from FIG. 3. This device is cut out from a block of cellular plastics.

A groove 50,52 is made in the upper side 46 and underside 48, respectively, of the biting bit, these grooves being intended for locating the position of the teeth on the biting bit when it is bitten into. A slit 54 or 56, respectively, opens into the bottom of each respective groove, said slit extending along the whole length of the biting bit and having a depth allowing the teeth to bite down so deeply into the slit that the gum around the teeth will come into engagement against the upper side and underside of the biting bit, as is schematically shown in FIG. 4. The gum will thereby be subjected to a healthy massage during chewing in the slits. The two teeth in FIG. 4 are denoted by 58,60 and the associated gum by 62,64. The arrow 66 indicates an upwards and downwards chewing motion for the tooth 58 such that the latter executes such motion in the slit 54.

The opposing side walls of the slit 54 are denoted by 54a, 54b and the opposing side walls of the slit 56 by 56a,56b.

The slits 54,56 are made in the biting bit by a cutting process so that the two opposing side walls in the respective slit will have the general surface structure shown and explained in conjunction with FIGS. 1, 2 and 2A.

When the teeth 58,60 chew up and down in the slits 54,56, the cleaning effect on the teeth thus obtained has shown to be satisfactory in practical tests.

FIGS. 8 and 9 illustrate how the biting bit 44 is intended to be moved along the upper 66 and lower 68 row of teeth into different positions. It is apparent from these figures that the length of the biting bit in this case is smaller than the length of half the row of teeth 66 and 68, which makes it possible to use slits which are substantially straight. If the bit is longer, the respective slit should have a curved shape approximately suiting the row of teeth.

If so desired, the biting bit can be prepared with a certain amount of antiseptic material or liquid having a purifying, antibacterial or anti-odour effect.

The handle 46 is connected to the inside 70 of the biting bit in the example shown. The outside 72 of the biting bit can be formed with a projection (not shown) so made that the tongue can be pressed against this projection obliquely upwards or obliquely downwards to keep the biting bit pressed against the upper or lower row of teeth when only the lower or upper row of teeth, respectively, is to carry out a chewing motion in its slit.

A cleaning device according to FIG. 3 is shown in FIG. 7, with the difference that the slit 54s and 56s, respectively, is zigzag-shaped or corrugated, so that corresponding ridges and intermediate valleys are obtained at the cut surfaces to provide improved adjustment to the convex surfaces of the teeth.

The cleaning device as shown in FIGS. 3 and 7 can be manufactured in a simple way, as is apparent from FIGS. 5 and 6. In a cellular plastics web having a rectangular cross-section, two recesses 72,73 are cut out, the widths of which correspond to the length of the handle 46. These recesses leave a material layer 76' corresponding to the thickness of the handle. The remaining edge portions 76,78 of the web form the starting material of the biting bits 44. Grooves 50,52 are cut in the portions 76,78 and slits 54,56 are cut into these grooves.

The web thus obtained can now be divided into individual cleaning means 42 by being parted along a transverse cutting plane 80, as well as a cutting plane 82 determining the shape of the front edge 46a of the handle, as shown in FIG. 3. By forming the cutting plane 82 symmetrically in relation to a central plane halfway between two adjacent cutting planes 80, two cleaning devices in reversed relationship are obtained between the cutting planes 80, as is apparent from FIG. 5. The handles 46 will then be displaced towards one end of the biting bit, which facilitates the insertion of the biting bit to the sides in the mouth, as will be appreciated after studying FIGS. 8 and 9.

For some cellular plastics materials it can be suitable to have more or less narrow grooves instead of slits, although these grooves have approximately the same depth as the slits.

The biting bit 81 in FIGS. 10-12 has two grooves 82,82a with opposing side walls 83,84 extending to the bottom 85 of the respective groove. The biting bit consists of the same material as referred to above, and thus the side walls 83,84 will serve as scrubbing means when the teeth are chewed in the grooves. The sides 83,84 are inclined so that the mouth 86 to the groove 82 is narrower than the width of the groove at its bottom 85. Accordingly, the edges 87,88 of the groove will scrub along the teeth in an efficient manner and the groove, widening towards its bottom, will permit teeth of varying sizes and at different angles to enter the groove.

Furthermore, there are a plurality of transverse slits 89 across the groove and extending deeper and wider in the groove as seen in FIG. 12. The side walls of the groove 82 will be divided by the slits 89 into separate scrubbing portions 90 which will act as individual brushes. The scrubbing portions 90 will adjust their position to a certain extent to the individual shape of the tooth they engage.

The cleaning device according to the invention can be made in still further different ways within the scope of the accompanying claims.

What I claim is:

1. A tooth-cleaning device with a biting bit having two opposing side walls to receive therebetween a plurality of teeth while biting the teeth together over the biting bit, the device comprising a head and a transverse handle projecting from one side of the head, the head and handle being integral with each other and both being of resilient cellular material, tooth-receiving grooves extending lengthwise of the head on opposite sides of the head, the cross-sectional configuration of the grooves widening toward the bottom of the grooves, the side walls of the grooves being lined with cut-through cells of the cellular material of the head thereby to provide a multiplicity of cleaning surfaces on the side walls of each groove, and a plurality of transverse slits crossing the grooves and dividing the opposite walls of each groove into a number of individually flexible portions so as to facilitate adjustment to the individual teeth.

2. A device as claimed in claim 1, the handle being located at one end only of the head and extending from the head in a direction perpendicular to a plane that includes both of the grooves.

* * * * *